United States Patent [19]

Fields, Jr. et al.

[11] Patent Number: 4,937,376

[45] Date of Patent: Jun. 26, 1990

[54] PROCESS FOR PRODUCING N-PHOSPHONOMETHYLGLYCINE

[75] Inventors: Donald L. Fields, Jr., Manchester; Raymond C. Grabiak, Maryland Heights; Dennis P. Riley, Ballwin, all of Mo.

[73] Assignee: Monsanto Company, St. Louis, Mo.

[21] Appl. No.: 356,484

[22] Filed: May 25, 1989

[51] Int. Cl.$^5$ ............................................... C07F 9/38
[52] U.S. Cl. ..................................................... 562/16
[58] Field of Search ........................................... 562/16

[56] References Cited

U.S. PATENT DOCUMENTS

| | | | |
|---|---|---|---|
| 3,950,402 | 4/1976 | Franz | 260/502.5 |
| 3,954,848 | 5/1976 | Franz | 260/502.5 |
| 3,969,398 | 7/1976 | Hershman | 260/502.5 |
| 4,853,159 | 8/1989 | Riley et al. | 562/17 |

FOREIGN PATENT DOCUMENTS 011706  1/1981  Hungary.

OTHER PUBLICATIONS

*Kirk–Othmer Encyclopedia of Chemical Technology*, 2nd Ed. vol. 16, pp. 899–913 (1968).

*Primary Examiner*—J. E. Evans
*Attorney, Agent, or Firm*—Frank D. Shearin

[57] ABSTRACT

A process for the production of N-phosphonomethylglycine comprising contacting N-phosphonomethyliminoacetic acid with a molecular oxygen-containing gas in the presence of a catalyst selected from the group consisting of the salts and salt complexes of manganese, cobalt, iron, nickel, chromium, ruthenium, aluminum, molybdenum, vanadium and cerium, and an effective amount of a quinone or hydroquinone.

14 Claims, No Drawings

PROCESS FOR PRODUCING N-PHOSPHONOMETHYLGLYCINE

BACKGROUND OF THE INVENTION

This invention relates to a process for preparing N-phosphonomethylglycine by the oxidation of N-phosphonomethyliminodiacetic acid using a homogeneous catalyst system. More particularly, this invention relates to a process for producing N-phosphonomethylglycine by the oxidation of N-phosphonomethyliminodiacetic acid using a salt of a selected metal in the presence of a quinone or quinone derivative.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-Phosphonomethylglycine and its salts are conveniently applied in an aqueous formulation as a postemergent phytotoxicant for the control of numerous plant species. N-Phosphononmethylglycine and its salts are characterized by broad spectrum activity, i.e., the controlled growth of a wide variety of plants.

Numerous methods are known in the art for the oxidation of the N-phosphonomethyliminodiacetic acid to N-phosphonomethylglycine. For example, U.S. Pat. No. 3,969,398 to Hershman discloses a process for the production of N-phosphonomethylglycine by the oxidation of N-phosphonomethyliminodiacetic acid utilizing a molecular oxygen-containing gas as the oxidant in the presence of a catalyst consisting essentially of activated carbon. U.S. Pat. No. 3,950,402 discloses a method where N-phosphonomethyliminodiacetic acid is oxidized to N-phosphonomethylglycine in an aqueous media using a free oxygen-containing gas and a nobel metal catalyst, such as palladium, platinum or rhodium on a support. U.S. Pat. No. 3,954,848 discloses the oxidation of N-phosphonomethyliminodiacetic acid with hydrogen peroxide and a acid such as sulfuric acid. Hungarian Patent Application No. 011706 discloses the oxidation of N-phosphonomethyliminodiacetic acid with peroxide in the presence of metals or metal compounds.

The quinone and quinone derivatives useful in the process of the present invention are known to those skilled in the art to be useful for their biological properties, as dyes, and for their redox properties (see for example *Kirk-Othmer Encyclopedia of Chemical Technology*, Second Edition, Vol. 16, pp 899–913, John Wiley & Sons (1968).

Although satisfactory results are obtained by the processes of the prior art to prepare N-phosphonomethylglycine using heterogeneous catalysts such as activated carbon or a noble metal on a support, there is now provided a process for preparing N-phosphonomethylglycine using a homogeneous catalyst system which produces outstanding results through high conversions and selectivities, which minimizes the formation of undesirable by-products such as phosphate and simplifies the separation of the product from the catalyst. The process of the present invention also achieves these results at lower pressures than the processes of the prior art.

SUMMARY OF THE INVENTION

These and other advantages are achieved by a process for the production of N-phosphonomethylglycine comprising contacting N-phosphonomethyliminodiacetic acid with a molecular oxygen-containing gas in the presence of a catalyst selected from the group consisting of the salts and salt complexes of manganese, cobalt, iron, nickel, chromium, ruthenium, aluminum, vanadium and cerium, and an effective amount of a quinone or quinone derivative represented by the formulas

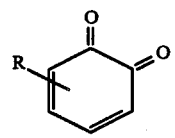

1

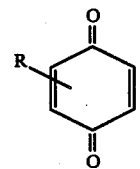

2

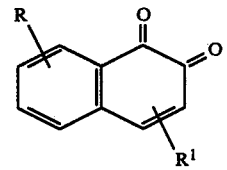

3

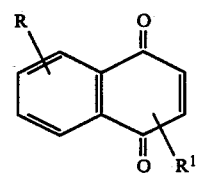

4

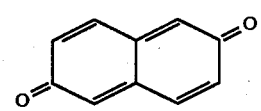

5

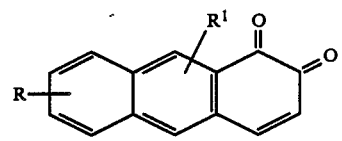

6

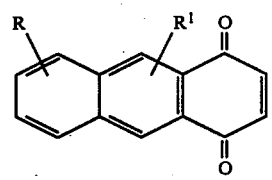

7

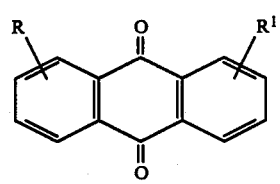

8

-continued
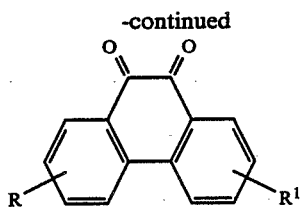
9
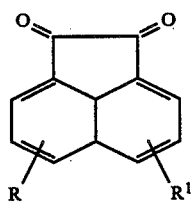
10
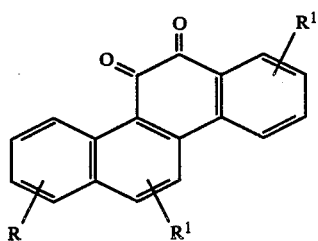
11
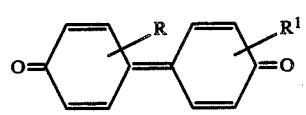
12
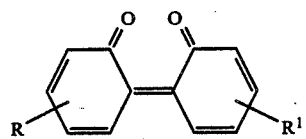
13
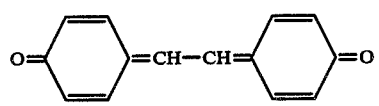
14
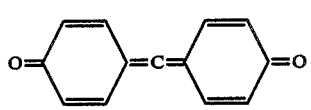
15
and the corresponding hydroquinones represented by the formulas
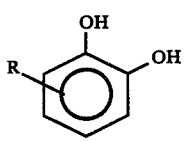
16
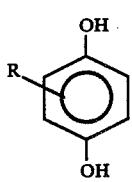
17
-continued
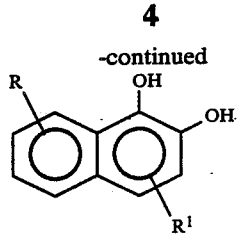
18
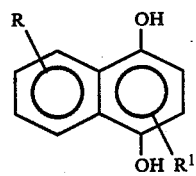
19
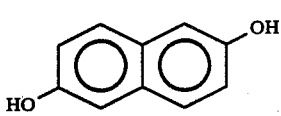
20
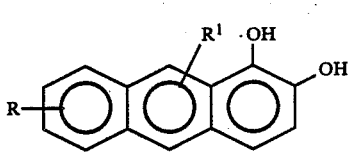
21
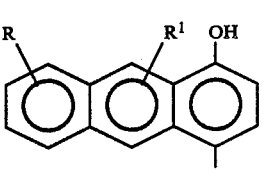
22
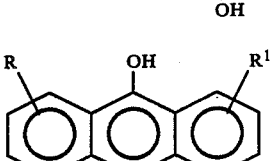
23
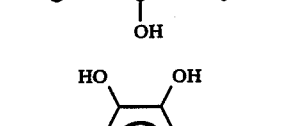
24
25
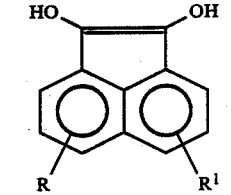
26
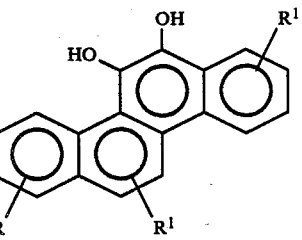

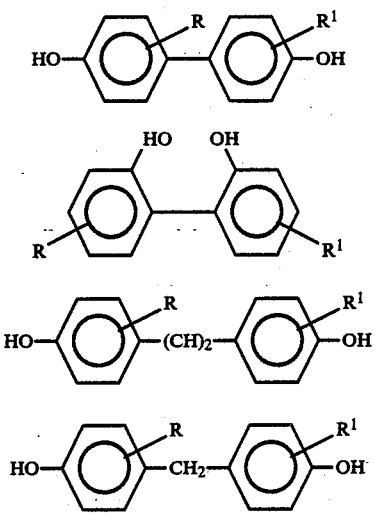

wherein R and $R^1$ are groups to solubilize the quinone or hydroquinone in the reaction medium.

DETAILED DESCRIPTION OF THE INVENTION

The process of the present invention involves contacting N-phosphonomethyliminodiacetic acid in a slurry or solution with a water soluble salt or a salt complex of selected metals in the presence of a quinone or hydroquinone. The mixture or solution is contacted with a molecular oxygen-containing gas while heating the reaction mass to a temperature sufficiently high to initiate and sustain the oxidation reaction of N-phosphonomethyliminodiacetic acid to produce N-phosphonomethylglycine.

The catalyst in the present invention can be any one or more of the salt and salt complexes of manganese, cobalt, iron, nickel, chromium, ruthenium, aluminum, molybdenum, vanadium or cerium. Suitable salts include manganese acetate, manganese sulfate, manganese(II or III) acetylacetonate, cobalt sulfate, cobalt-(II or III) acetylacetonate, cobalt chloride, cobalt bromine, cobalt nitrate, cobalt acetate, ceric ammonium sulfate, ceric ammonium nitrate, ferric ammonium sulfate, and salts such as nickel bromide, chromium chloride, ruthenium chloride, ruthenium bromide, aluminum nitrate, vanadium sulfate, vanadium bromide, vanadium chloride, and the like. It is preferred to use salts of manganese, cobalt, vanadium or cerium, and cobalt and vanadium salts are especially preferred.

The catalyst can be added to the N-phosphonomethyliminodiacetic acid in the salt form, or the salt may be generated in situ by the addition of a source of the metal ion, such as manganese dioxide, cobalt oxide or vanadium pentoxide which dissolves in the reaction mixture.

The concentration of the catalyst in the process of the present invention can vary within wide limits. The concentration can vary between about 1 molar to about 0.0001 molar total metal ion concentration. For most of the metal salts, the reaction appears to have a first order dependency on the catalyst concentration, i.e. the reaction rate increases linearly as a catalyst concentration increases. The preferred concentration for the catalyst metal ion is in the range of about 0.1 molar to about 0.001 molar which gives a suitably fast rate of reaction that can be easily controlled and favors selectivity to N-phosphonomethylglycine.

The quinone and quinone derivatives of the present invention are known in the art. Suitable water soluble quinone compounds include, hydroxy substituted p-benzoquinone, o-benzoquinone, p-benzoquinone, 1,4-naphthoquinone, 1,2-naphthoquinone, 2,6-naphthoquinone, 1,4,5,8-naphthodiquinone. Compounds that have been substituted with appropriate substituents to make them water soluble in the reaction mixture include dihydroquinones, stilbenequinones, 9,10-phenanthrenequinones, 1,4-phenanthrenequinones, 1,2-phenanthrenequinones, 3,4-phenanthrenequinones, 9,10-anthraquinones, 1,2-anthraquinones, 1,4-anthraquinones, 1,2-benz-9,10-antraquinone(benz-[a]anthracene-7,12-dione)s, 1,2-benz-3,4-anthraquinone (benz[a]anthracene-5,6-dione)s, 1,2,5,6-dibenz-9,10-anthraquinone(dibenz[a,h]anthracene-7,14-dione)s, 5,6-chrysenequinone (5,6-chrysenedione)s, and 6,12-chrysenequinone(6,12-chrysenedione)s.

As will occur to those skilled in the art in view of the present disclosure, quinones or hydroquinones that are substituted on at least one of the ring structures can be used in the process of the present invention, provided that the substituted group does not interfere with the process of the present invention. Examples of groups that can be substituted on the ring structures include: halo such as chloro or bromo; sulfonyl groups; alkyl having from one to six carbon atoms; oxyalkyl having from one to six carbon atoms; benzyl; amino, carboxy, cyano, nitro, hydroxy, phosphonic, phosphinic, phosphonium, quaternary amino groups, and the like. However, higher molecular weight quinones and hydroquinones, and anthraquinones and anthrahydroquinones, can be insoluble in the aqueous reaction medium. Accordingly, such higher molecular weight compounds, such as the anthraquinones, require substitution of a water solubilizing functional group on the molecule to aid water solubility as known to those skilled in the art. Of these, naphthaquinone, substituted anthraquinones and benzoquinones are preferred, and sulfonyl acid anthraquinone derivatives substituted with sulfonic acid groups and salts thereof are especially preferred. Other preferred compounds include 4-naphthalenediol and a sulfonic acid salt of 9,10-anthracenediol.

The concentration of the quinone and hydroquinone compounds in the process of the present invention can vary within wide limits, depending upon the catalyst salt and the amount of N-phosphonomethyliminodiacetic acid that are used, and the particular quinone or hydroquinone compound that is selected. In general, it has been found that the concentration of the quinone and hydroquinone compounds can vary from about 0.005 molar in the reaction solution to one molar, and higher concentrations of the quinone and hydroquinone compounds compound can be used, although such higher concentrations do not seem to have a significant effect on the selectivity of the oxidation of N-phosphonomethyliminodiacetic acid to N-phosphonomethylglycine. It has been found that concentrations of the quinone and hydroquinone compounds between about 0.01 molar to about 0.5 molar provides satisfactory results, and this is the concentration that is preferred.

The reaction temperature is sufficient to initiate and sustain the oxidation reaction and can vary from about 25° C. to 150° C. In general, as the reaction temperature increases, the reaction rate increases. To achieve an easily controlled reaction rate and favor selectivity of the reaction to the formation of N-phosphonomethylglycine, a preferred temperature range is from about 50° C. to about 90° C. If temperatures above the boiling point are used, pressure should be maintained on the reaction system.

To carry out the process of the present invention, it is only necessary to bring N-phosphonomethyliminodiacetic acid together with an effective amount of the catalyst salt and an effective amount of the quinone or hydroquinone compounds in the presence of a molecular oxygen-containing gas in an aqueous solution or slurry. The term "molecular oxygen-containing gas" means molecular oxygen gas or any gaseous mixture containing molecular oxygen with one or more diluents which are nonreactive with the oxygen or with the reactants or the products under the conditions of the reaction. Examples of each diluent gases include air, helium, argon, nitrogen, or other inert gases, or oxygen-hydrocarbon mixtures. A preferred molecular oxygen-containing gas is undiluted oxygen gas.

The oxygen concentration, i.e., the partial pressure of oxygen, affects the reaction rate and selectivity to the desired N-phosphonomethylglycine. As the partial pressure of oxygen increases, the reaction rate generally increases. When the partial pressure of oxygen is below about $6.89 \times 10^3$ N/m$^2$ (30 psig) the reaction is somewhat slow, and we prefer to use at least this partial pressure of oxygen. Although there is no upper limit to the partial pressure of oxygen, we have found that satisfactory results can be achieved at a partial pressure of oxygen up to $3.45 \times 10^6$ N/m$^2$ (500 psig).

As will occur to those skilled in the art in view of the present disclosure, the manner in which the aqueous solution or slurry of N-phosphonomethyliminodiacetic acid is contacted with a molecular oxygen-containing gas in the presence of the metal salt catalyst and the quinone or hydroquinone compounds can vary greatly. For example, the N-phosphonomethyliminodiacetic acid solution can be contacted with the oxygen-containing gas by agitation, such as bubbling, stirring, shaking, and the like. The process of the present invention only requires actively contacting the molecular oxygen-containing gas with the aqueous solution or mixture of N-phosphonomethyliminodiacetic acid containing the metal catalyst salt and the quinone or hydroquinone compounds.

The initial pH of the reaction affects the reaction rate and the selectivity of N-phosphonomethylglycine. The initial pH of the reaction can vary between about pH 0.1 to about pH 7. A preferred range is from about pH 0.1 to pH 3, and a more preferred pH range is the natural pH of the N-phosphonomethyliminodiacetic acid in an aqueous solution which varies with the N-phosphonomethyliminodiacetic acid concentration and the reaction temperature.

The oxidation reaction can take place in a solution or a slurry. For a solution, the initial concentration of the N-phosphonomethyliminodiacetic acid in the reaction mass is a function of the solubility of the N-phosphonomethyliminodiacetic acid in the solvent (i.e. water) at both the desired reaction temperature and the initial pH of the solution. As the solvent temperature and the initial pH change, the solubility of N-phosphonomethyliminodiacetic acid changes. It has been found that the process of the present invention works with very little dilute solutions or even with a slurry of the N-phosphonomethyliminodiacetic acid in an aqueous solution. The reaction is typically carried out in an aqueous solvent, i.e., containing at least about 50 wt.% water. The preferred aqueous solvent is distilled, deionized water.

The invention is further illustrated by, but not limited to, the following examples. In all cases the reactions were conducted in an Engineers 100 ml autoclave in which a stirrer was installed in the head as were three additional valve ports that were used as a sample port, a gas inlet and purged gas outlet. The stirrer maintained sufficient agitation to afford thorough gas liquid mixing. The indicated amount of catalyst salt and quinone or hydroquinone compound was dissolved or suspended in a distilled deionized water solution containing the indicated amounts of N-phosphonomethyliminodiacetic acid. The reactor was sealed, pressurized to $3.1 \times 10^6$ N/m$^2$ (450 psig) unless otherwise indicated with an oxygen gas sweep at about 300 cc per minute, and heated to the indicated reaction temperatures with agitation.

The percent selectivity to N-phosphonomethylglycine was determined by dividing the moles of N-phosphonomethylglycine and N-formyl-N-phosphonomethylglycine produced by the total moles of N-phosphonomethyliminodiacetic acid consumed and multiplying by 100. The percent conversion of N-phosphonomethyliminodiacetic acid was determined by dividing the moles of N-phosphonomethyliminodiacetic acid that were reacted by the total moles of starting N-phosphonomethyldiacetic acid and multiplying by 100.

EXAMPLES 1-6

Into the autoclave was added water (100 ml), N-phosphonomethyliminodiacetic acid (26.7 g) and cobalt sulfate (3.3 g). Except for Example 1 a quinone compound (0.5 g) was used). The reactions were run at 95° C. for three hours in all Examples. The results are shown in Table 1.

TABLE 1

| Example | Benzoquinones | Selectivity % | Conversion % |
|---|---|---|---|
| 1 | None | 61.6 | 99.9 |
| 2 | (tetrachloro-1,4-benzoquinone) | 86.5 | 19.3 |
| 3 | (tetrahydroxy-1,4-benzoquinone) | 63.6 | 99.5 |
| 4 | (2,5-dihydroxy-1,4-benzoquinone) | 64.6 | 99.7 |

TABLE 1-continued

| Example | Benzoquinones | Selectivity % | Conversion % |
|---|---|---|---|
| 5 | (2,3-dichloro-5,6-dicyano-1,4-benzoquinone) | 72.9 | 95.5 |
| 6 | (2,5-dichloro-3,6-dihydroxy-1,4-benzoquinone) | 65.0 | 98.6 |

EXAMPLES 7–12

The procedure of Examples 1–6 was repeated except that napthaquinones were used. The results are shown in Table 2.

TABLE 2

| Example | Napthaquinones | Selectivity % | Conversion % |
|---|---|---|---|
| 7 | None | 61.6 | 99.9 |
| 8 | (1,4-naphthoquinone) | 73.1 | 87.3 |
| 9 | (NaO₃S-, OH, OH substituted naphthoquinone) | 69.8 | 99.5 |
| 10 | (5,8-dihydroxy-1,4-naphthoquinone) | 67.4 | 98.2 |
| 11 | (SO₃Na substituted naphthoquinone) | 75.5 | 40.0 |
| 12 | (1,4-dihydroxynaphthalene) | 66.1 | 96.0 |

EXAMPLES 13–17

The procedure of Examples 1–6 was repeated except that anthraquinones were used instead of benzoquinones. The results are shown in Table 3.

TABLE 3

| Example | Anthraquinone | Selectivity % | Conversion % |
|---|---|---|---|
| 13 | None | 61.6 | 99.9 |
| 14 | (2,6-disulfonate anthraquinone) | 67.4 | 98.1 |
| 15 | (1-sulfonate anthraquinone) | 68.7 | 99.4 |
| 16 | (2-sulfonate anthraquinone) | 66.0 | 99.5 |
| 17 | (1,5-disulfonate anthraquinone) | 65.7 | 97.2 |

EXAMPLES 18–22

Into the 300 ml autoclave was added water (125 ml), 20.44 g of N-phosphonomethyliminodiacetic acid, and cobalt bromide hexahydrate (1.47 g). Except for reaction 18 an anthraquinone derivative was used. The reactions were run at 95° C. under $1.38 \times 10^6$ N/m² (200 psig) oxygen pressure.

| Example | Anthraquinone | Time (hrs) | % Selectivity | % Conversion |
|---|---|---|---|---|
| 18 | none | 2 | 63.2 | 91.2 |
| 19 | 0.70 g of the anthraquinone of example 15 | 3 | 79.3 | 96.6 |
| 20 | 0.70 g of the anthraquinone H₂O of example 16 | 2.25 | 79 | 90.2 |
| 21 | 1.031 g of the anthraquinone of example 14 | 2.25 | 75.8 | 87.9 |
| 22 | 1.10 g of the anthraquinone H₂O of example 17 | 2.5 | 72.6 | 90.1 |

EXAMPLE 23

A. Into the autoclave was added water (100 ml) N-phosphonoiminodiacetic acid (27 g) and vanadyl sulfate dihydrate (1.6 g). The autoclave was heated to 80° C. for one hour. Analysis indicated that the conversion was 97.7% and the selectivity was 52.2%

B. The procedure of part A was repeated except that 0.5 g of an anthraquinone represented by the formula

[Structure 5: anthraquinone-1-sulfonate sodium salt]

was added to the autoclave. Analysis indicated that the conversion was 67.9% and the selectivity was 74.1%.

Although the invention has been described in terms of specified embodiments, which are set forth in considerable detail, it should be understood that this by way of illustration only, and that alternative embodiments and operating techniques will become apparent for those skilled in the art in view of the disclosure. For example, other quinone and hydroquinone compounds not specifically disclosed in the text hereof can be used in the process of the present invention provided that they do not cause a deleterious effect on the selectivity to N-phosphonomethylglycine. Accordingly, modifications can be made without departing from the spirit of the described invention.

What is claimed is:

1. A process for the production of N-phosphonomethylglycine comprising contacting N-phosphonomethyliminoacetic acid with a molecular oxygen-containing gas in the presence of a catalyst selected from the group consisting of the salts and salt complexes of manganese, cobalt, iron, nickel, chromium, ruthenium, aluminum, vanadium and cerium, and an effective amount of a quinone or quinone derivative represented by the formulas:

[Structures 1–14 shown]

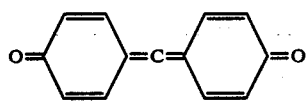

and the corresponding hydroquinones:

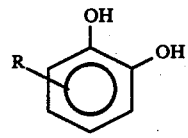 16

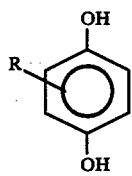 17

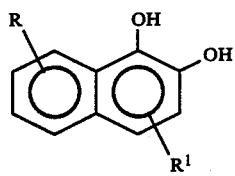 18

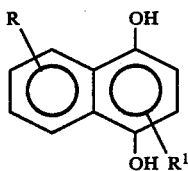 19

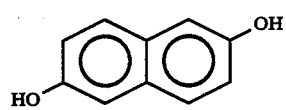 20

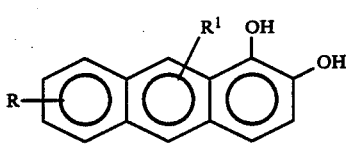 21

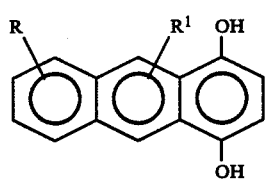 22

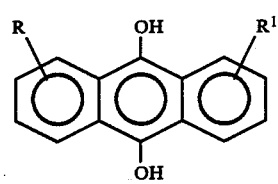 23

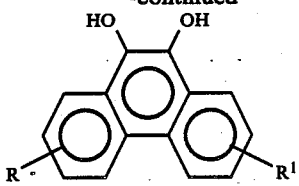 24

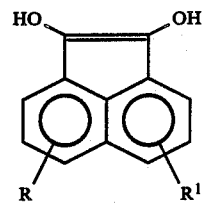 25

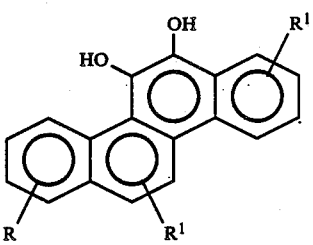 26

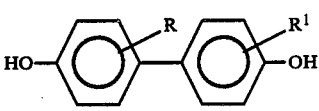 27

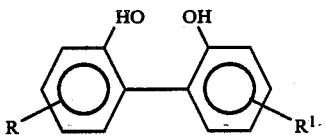 28

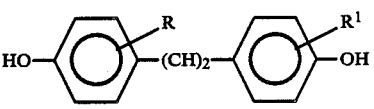 29

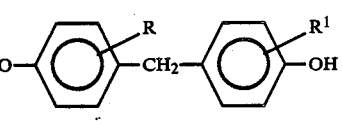 30 wherein R and $R^1$ are groups to solubilize the quinone or hydroquinone in the reaction medium.

2. A process of claim 1 wherein R and $R^1$ are individually selected from the group consisting of hydrogen, halo, sulfonyl, nitro, cyano, quaternary amino groups, hydroxy, carboxy, amino, phosphonic, phosphinic, phosphonium, provided that both R and $R^1$ cannot be hydrogen.

3. A process of claim 1 wherein the concentration of the quinone or quinone derivative is at least 0.01 molar.

4. A process of claim 3 wherein the catalyst salt concentration is between 0.1 molar and 0.001 molar total metal ion concentration.

5. A process of claim 1 wherein the quinone or quinone derivative is selected from the group consisting of benzoquinone, anthraquinone, napthaquinone and hydroquinone.

6. A process of claim 5 wherein the quinone or quinone derivative is benzoquinone.

7. A process of claim 5 wherein the quinone or quinone derivative is a water soluble anthraquinone.

8. A process of claim 7 wherein the anthraquinone is sulfonated anthraquinone.

9. A process of claim 5 wherein the catalyst is selected from the group consisting of the salts of cobalt, manganese, vanadium and cerium.

10. A process of claim 9 wherein the catalyst is a vanadium salt.

11. A process of claim 9 wherein the catalyst is a cobalt salt.

12. A process of claim 9 wherein the concentration of the quinone or quinone derivative is at least 0.01 molar.

13. A process of claim 10 wherein the catalyst salt concentration is between 0.1 molar and 0.5 molar total metal concentration.

14. A process of claims 1 or 13 wherein the N-phosphonomethyliminodiacetic acid is present as a slurry.

* * * * *